(12) United States Patent
Burkhart

(10) Patent No.: US 8,202,297 B2
(45) Date of Patent: Jun. 19, 2012

(54) TECHNIQUE FOR TISSUE FIXATION BY REELING IN AND ANCHORING SUTURE ATTACHED TO TISSUE

(75) Inventor: Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 266 days.

(21) Appl. No.: 12/488,356

(22) Filed: Jun. 19, 2009

(65) Prior Publication Data

US 2009/0318965 A1 Dec. 24, 2009

Related U.S. Application Data

(60) Provisional application No. 61/074,111, filed on Jun. 19, 2008.

(51) Int. Cl.
*A61B 17/04* (2006.01)

(52) U.S. Cl. ........................................................ 606/232

(58) Field of Classification Search .................. 606/139, 606/144, 228, 232, 300, 301, 224
See application file for complete search history.

(56) References Cited

U.S. PATENT DOCUMENTS

| | | | | |
|---|---|---|---|---|
| 5,891,168 A | * | 4/1999 | Thal | 606/232 |
| 6,267,766 B1 | | 7/2001 | Burkhart | |
| 6,527,795 B1 | * | 3/2003 | Lizardi | 606/232 |
| 6,540,750 B2 | | 4/2003 | Burkhart | |
| 2007/0135843 A1 | * | 6/2007 | Burkhart | 606/232 |
| 2007/0191849 A1 | | 8/2007 | ElAttrache et al. | |
| 2008/0004659 A1 | | 1/2008 | Burkhart et al. | |
| 2008/0009904 A1 | * | 1/2008 | Bourque et al. | 606/232 |
| 2008/0208253 A1 | | 8/2008 | Dreyfuss et al. | |

OTHER PUBLICATIONS

"Athrex is Reaching New Heights in Rotator Cuff Repair." Athrex, Inc. 2007.*

* cited by examiner

*Primary Examiner* — Ryan Severson
*Assistant Examiner* — Katherine M Shi
(74) *Attorney, Agent, or Firm* — Dickstein Shapiro LLP

(57) ABSTRACT

A method and device for knotless fixation of tissue. The method utilizes a push-in type anchor (for example, a self-punching anchor) and a suture chain that includes a loop or a plurality of loops. A first portion of the suture chain is secured to the tissue to be fixated. The suture chain is next secured to the push-in type anchor (for example, by passing the suture chain through an eyelet of the anchor). The anchor is then advanced along the suture chain to bring a tip of the anchor above a chosen loop or link of the suture chain. The tip of the anchor is pushed through the chosen loop so that the tip locks the chosen loop in place (for example, by capturing both sides of the link above a shoulder of the anchor). With the captured link, the anchor is advanced into a pilot hole or socket formed in the bone, and then the anchor is rotated within the hole or socket to reel in the suture chain and to tension, therefore, the suture chain.

11 Claims, 5 Drawing Sheets

TECHNIQUE FOR TISSUE FIXATION BY REELING IN AND ANCHORING SUTURE ATTACHED TO TISSUE

CROSS-REFERENCE TO RELATED APPLICATIONS

This application claims the benefit of U.S. Provisional Application No. 61/074,111, filed Jun. 19, 2008, the entire disclosure of which is incorporated by reference herein.

FIELD OF THE INVENTION

The present invention relates to surgical fixation and, more particularly, to methods of conducting anatomical tissue repair, such as ligament repair and reconstruction, using a technique which involves reeling in and anchoring suture attached to tissue.

BACKGROUND OF THE INVENTION

When soft tissue such as a ligament or a tendon becomes detached from a bone, surgery is usually required to reattach or reconstruct the tissue. Often, a soft tissue graft is attached to the bone to facilitate re-growth and permanent attachment. Various fixation devices, including sutures, screws, staples, wedges, and plugs have been used in the past to secure soft tissue to bone. For example, in typical interference screw fixation, the graft is fixed to the bone by driving the screw into a blind hole or a tunnel in the bone while trapping the end of the graft between the screw and the bone tunnel. In other methods, the soft tissue graft is simply pinned against the bone using staples or sutures tied around the end of the graft to the bone.

U.S. Application Publ. No. 2008/0208253, the disclosure of which is incorporated by reference herein, discloses a surgical technique and associated instruments for securing soft tissue to bone which does not require the surgeon to tie suture knots to secure the tissue to the bone. According to this technique, a cannulated plug or screw is pre-loaded onto a distal end of a cannulated driver provided with an eyelet implant at its distal end. A suture attached to the graft is passed through the eyelet of the implant located at the distal end of the driver. The distal end of the driver together with the eyelet implant is inserted into bone (if the implant is self-punching) or is inserted into the bottom of a pre-formed hole, with the screw or plug disposed just outside the hole. Tension is applied to the suture to position the graft at the desired location relative to the bone hole. The screw or plug is then fully advanced into the pilot hole by turning the interference screw or tapping the plug until the cannulated screw or plug securely engages and locks in the eyelet implant, so that the cannulated plug or screw with the engaged eyelet implant is flush with the bone.

U.S. Application Publ. No. 2008/0004659, the disclosure of which is incorporated by reference herein, discloses a method, namely, swivel anchor technique, and device for knotless fixation of tissue. In this technique, a swivel anchor having a rotatable forked anchor tip is used to capture suture for surgical tissue repair without requiring suture knots. Tension on the repair constructs is adjustable through the selection of a specific chain link or links of the suture chain captured by a forked anchor tip of the swivel anchor. The swivel anchor is secured in a hole in bone by advancing a fixation device, such as a cannulated interference screw, over the body of the anchor.

U.S. Pat. Nos. 6,267,766 and 6,540,750, the disclosures of which are incorporated by reference herein, disclose a threaded suture anchor and method for anchoring suture to bone. The suture attached to tissue is passed through a hole in the anchor, and the anchor is then turned to reel-in the suture and the tissue attached to the suture, while also simultaneously seating the threaded suture anchor into bone.

Although the above-described techniques provide an improved method of graft fixation to bone through knotless fixation, it would be desirable to provide, in situ, an easy and adjustable way of tensioning a suture, and getting a hard stop on the suture without relying on friction. Accordingly, there exists a need in the art for an improved technique for knotless tissue fixation.

SUMMARY OF THE INVENTION

The present invention fulfills the needs noted above by providing a knotless tissue fixation technique by capturing and anchoring a link of suture chain attached to tissue. The technique of the present invention utilizes a push-in type anchor (for example, a self-punching anchor) and a suture chain that includes a plurality of loops. A first portion of the suture chain is secured to the tissue to be fixated. The suture chain is next secured to the push-in type anchor (for example, by passing the suture chain through an eyelet of the anchor). The anchor is then advanced along the suture chain to bring a tip of the anchor above a chosen loop or link of the suture chain. The tip of the anchor is pushed through the chosen loop so that the tip locks the chosen loop in place (for example, by capturing both sides of the link above a shoulder of the anchor). With the captured link, the anchor tip is advanced into a pilot hole or socket formed in the bone to fixate the tissue. The anchor is then rotated to "reel in" the suture chain, to provide an easy and adjustable way to tension the suture chain. The anchor is then advanced into the bone socket above the anchor tip and the "reeled-in" suture.

The technique of the present invention may be employed with various methods of knotless fixation of tissue to bone. An exemplary double-row technique of the present invention includes the steps of: (i) placing a medial anchor pre-loaded with a suture chain that includes a plurality of loops; (ii) passing the suture chain through soft tissue (for example, rotator cuff tear); (iii) capturing a loop or link of the suture chain with a tip of an anchor (such as a self-punching Push-Lock SP™ anchor) so that the anchor locks in the chosen loop; (iv) rotating the anchor so that the suture chain is reeled-in and tensioned; and (v) laterally fixating the anchor with the captured loop of the tensioned suture chain into a lateral bone socket. The knotless technique provides a hard stop that will not slip (in addition to the standard frictional interference of the suture chain between the anchor and the bone) as opposed to the standard interference-fit techniques which rely primarily on friction for fixation.

These and other features and advantages of the present invention will become apparent from the following description of the invention that is provided in connection with the accompanying drawings and illustrated embodiments of the invention.

DETAILED DESCRIPTION OF THE PREFERRED EMBODIMENTS

Figure 1:
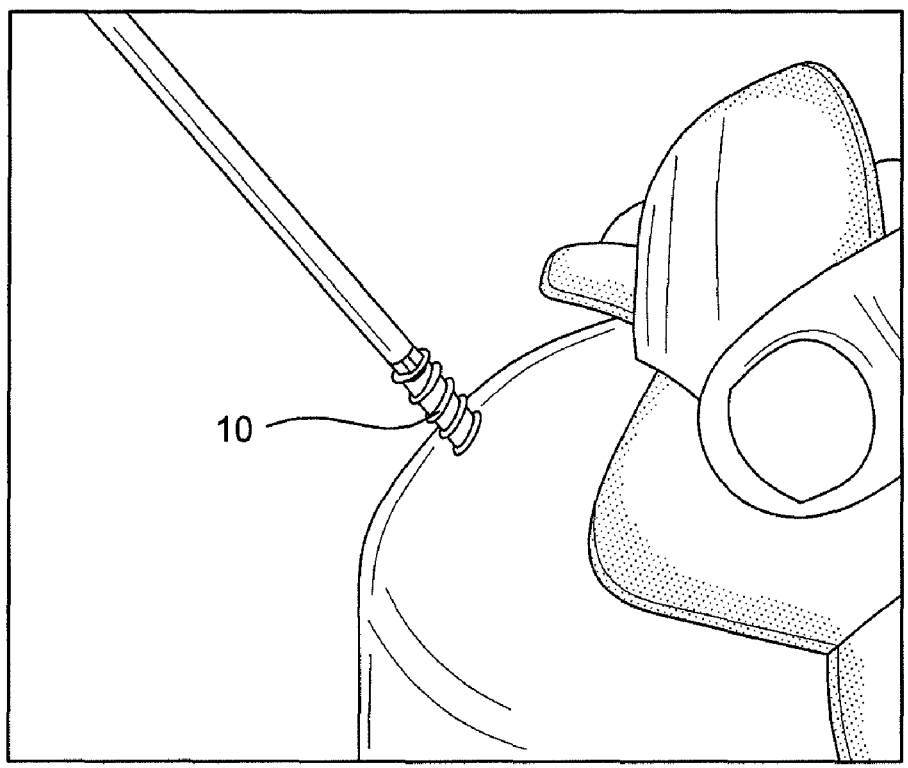
FIGS. 1-10 illustrate the technique of the present invention.

The present invention provides methods and apparatus for conducting anatomical tissue repair, such as ligament repair and reconstruction, using a technique in which suture attached to tissue is "reeled-in." The present invention utilizes a push-in type anchor (for example, a self-punching anchor) and a suture chain that includes a plurality of loops. A first portion of the suture chain is secured to the tissue to be fixated. The suture chain is next secured to the push-in type anchor (for example, by passing the suture chain through an eyelet of the anchor). The anchor is then advanced along the suture chain to bring a tip of the anchor above a chosen loop or link of the suture chain. The tip of the anchor is pushed through the chosen loop so that the tip locks the chosen loop in place (for example, by capturing both sides of the link above a shoulder of the anchor). With the captured link, the anchor is advanced into a pilot hole or socket formed in the bone to fixate the tissue. The anchor is then rotated to "reel in" the suture chain, to provide an easy and adjustable way to tension the suture chain and the tissue attached thereto.

The technique of the present invention may be used in various methods of fixation of soft tissue to bone. For example, an exemplary double-row technique (explained below with reference to FIGS. 1-8) includes the steps of: (i) providing a first medial row constructed with a first plurality of fixation devices, at least one of the first plurality of fixation devices being an anchor pre-loaded with a suture chain; (ii) passing the suture chain through soft tissue; (iii) securing the suture chain to a knotless fixation device (by threading the suture chain through an eyelet of the knotless fixation device, for example); (iv) capturing at least one link of the suture chain with a tip of the knotless fixation device; (v) fixating (into a lateral bone socket) the captured link and the knotless fixation device, to provide a second lateral row constructed with a second plurality of fixation devices, at least one of the second plurality of fixation devices being the knotless fixation device with the captured link; and (vi) rotating the knotless fixation device to reel-in the suture and tension, therefore, the suture chain. The suture chain extends over the soft tissue and is secured in place by the knotless fixation device.

The present invention provides a knotless suture fixation technique which utilizes a self-punching anchor along with a suture chain to "reel-lock" suture attached to tissue. This technique has elements of the various techniques described above (i.e., U.S. Patent Application Publ. No. 2008/0208253, U.S. Patent Application Publ. No. 2008/0004659, and U.S. Pat. Nos. 6,267,766 and 6,540,750), but combines these elements in a way which makes it superior to the prior techniques. One of the advantages of the technique of the present invention is that it is possible to easily adjust the suture chain tension. Further, it is possible to get a hard stop without relying on friction and to thread the suture chain through an anchor with the suture chain exiting through the same portal, so that a given link in the chain need not be captured inside the shoulder as in the swivel anchor technique.

According to an exemplary and illustrative embodiment only, pilot holes or sockets are created in the bone at the locations that the graft is to be secured. A suture anchor, preferably a fully threaded Bio-Corkscrew® preloaded with a FiberChain®, sold by Arthrex, Inc., Naples, Fla., is placed in a medial portal. The FiberChain® is passed through tissue using a suture passer, preferably a Scorpion™ Suture Passer, sold by Arthrex, Inc., Naples, Fla. The FiberChain® is pulled out through an anteriolateral portal and threaded through an eyelet of a self-punching PushLock SP™ anchor. The PushLock SP™ anchor is advanced along the FiberChain® and the PushLock SP™ anchor is turned, preferably in a clockwise direction, to bring the tip (i.e., the implant) of the PushLock SP™ anchor above a chosen link. Alternatively, the PushLock SP™ anchor may be advanced along the entire FiberChain®, without turning the PushLock SP™ anchor, but this results in greater friction on the FiberChain®.

The PushLock SP™ anchor tip is pushed through the chosen link to capture both sides of the link above the shoulder of the PushLock SP™ anchor tip so that the tip locks the chosen link in place. The FiberChain® link is securely captured above the shoulders of the tip of the self-punching PushLock SP™ anchor. The PushLock SP™ anchor tip is inserted into the bottom of the bone socket. The PushLock SP™ anchor is then rotated to "reel in" the FiberChain® and thereby provide an easy and adjustable way to tension the FiberChain®.

After the rotator cuff has been satisfactorily positioned by tensioning the FiberChain®, the PushLock SP™ anchor is advanced into the bone socket above the anchor tip, securing the fixation construct. Once the anchor is fully inserted and the FiberChain® is impacted into the pilot hole or socket, any loose ends of the FiberChain® protruding from the anchor site are then clipped short.

Referring now to the drawings, where like elements are designated by like reference numerals, FIGS. 1-10 illustrate the technique of the present invention under dry lab conditions. Details of the various instruments, accessories and implants used in the link-lock technique are listed below in Table 1.

TABLE 1

| List of Instruments, Accessories and Implants for the Reel-Lock Technique |
|---|
| PushLock SP anchor ™ |
| Description: The PushLock SP anchor was developed to help speed completion of a suture bridge while increasing the precision of the final construct. It combines a small titanium tip with either a PLLA or PEEK anchor body. The titanium tip minimizes the need to prepare a bone socket for the lateral row, where soft tissue can sometimes obscure the view. The self-punching feature helps maintain proper axial alignment of the anchor during its final insertion into the bone socket. |
| Bio-Corkscrew ® |
| Description: A bioabsorbable PLLA suture anchor that has 14 inch pounds of insertion torque strength. The strong internal drive mechanism provides double the resistance to stripping than any other bioabsorbable suture anchor available. |
| Bio-SwiveLock ™ C |
| Description: A 4.75 mm or 5.5 mm twist-in knotless anchor. This anchor functions very similar to the PushLock but with a twist-in design. This anchor is available with a bioabsorbable PLLA anchor body and PEEK |

TABLE 1-continued

List of Instruments, Accessories and Implants for the Reel-Lock Technique eyelet. It can be used as the lateral row of the suture bridge. It can also be combined with FiberTape ®.

Scorpion ™ Suture Passer

Description: Ergonomically designed for one-hand use, the multi-function suture passer can grasp rotator cuff tissue and retrieve a suture.

KingFisher ® Suture Retriever/Tissue Grasper

Description: It is used for arthroscopic tissue grasping/reduction and has a self-releasing jaw lock mechanism. To lock the jaws, and securely hold the tissue, pressure is applied on the posterior aspect of the forward finger. To release the lock, and open the jaws, finger pressure is transferred to the anterior portion of the forward ring.

FiberChain ®

Description: A single stranded #2 FiberWire ® suture strand that transitions to chain links of interwoven FiberWire ®. The FiberWire ® suture is a multi-stranded long chain ultra-high molecular weight polyethylene (UHMWPE) core with a braided jacket of polyester and UHMWPE.

FiberTape ®

Description: An ultra-high strength 2 mm tape using an ultrahigh molecular weight polyethylene structure.

Figure 2:
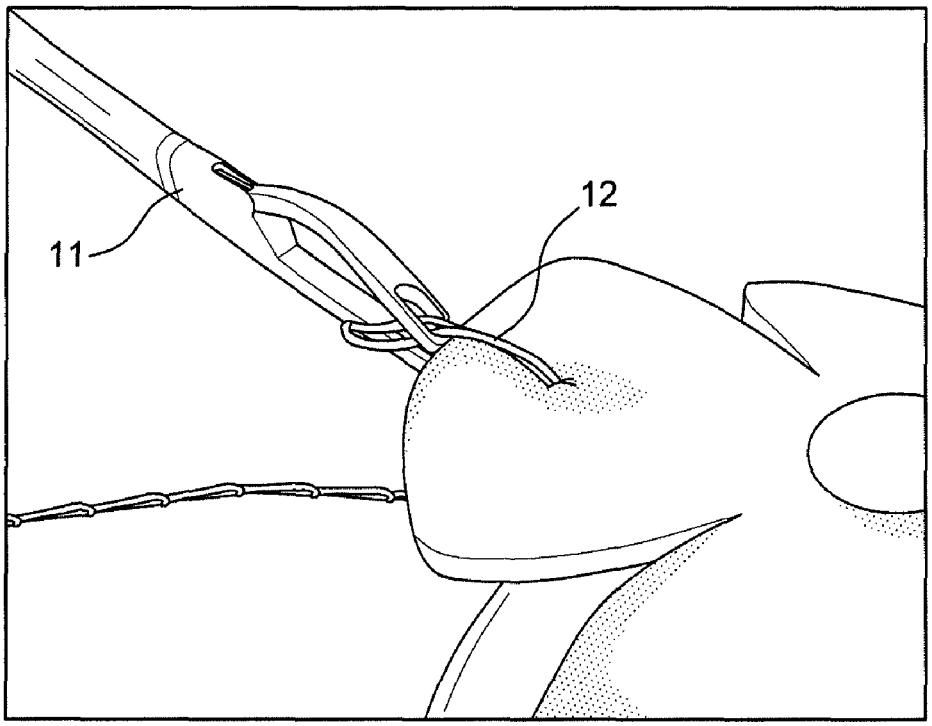
Figure 3:
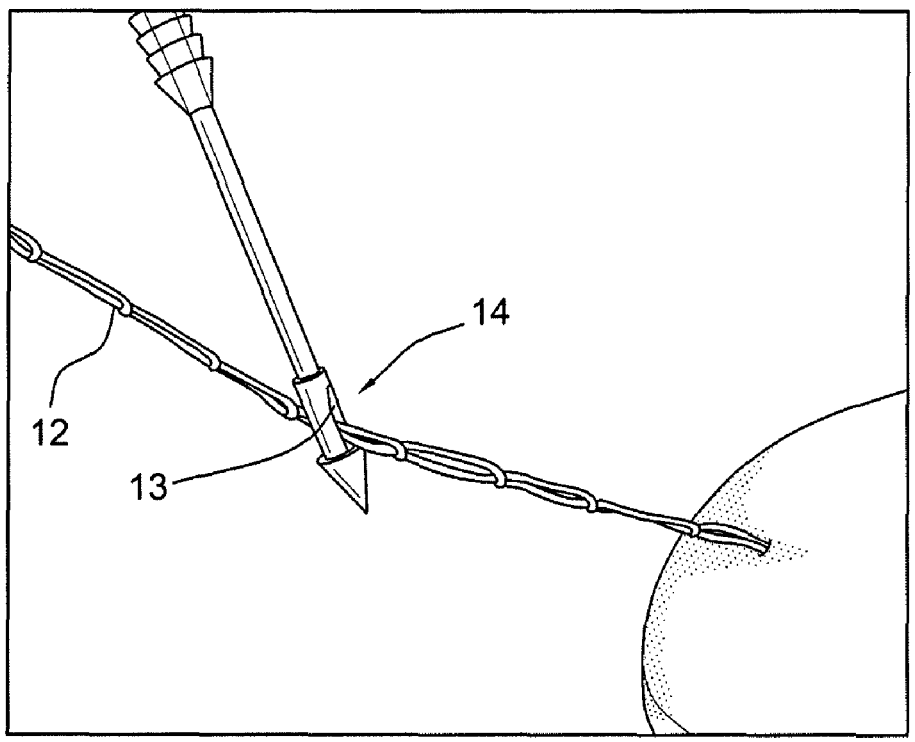

Referring to FIG. 1, an anchor 10, preferably a fully threaded Bio-Corkscrew® preloaded with FiberChain®, is placed in a medial portal. The FiberChain® 12 is passed using a Scorpion™ suture passer 11 and the FiberChain® 12 is pulled out through an anteriolateral portal, as shown in FIG. 2. The FiberChain® 12 is threaded through an eyelet 13 of a tip of a self-punching PushLock SP™ anchor 14, as shown in FIG. 3.

Figure 4:
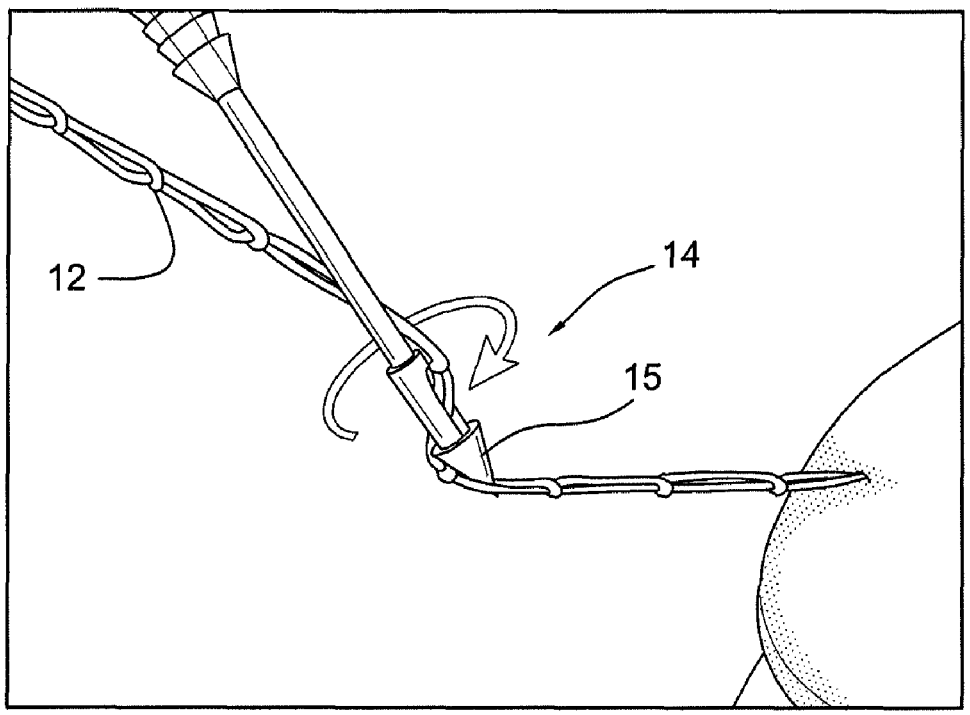
Figure 5:
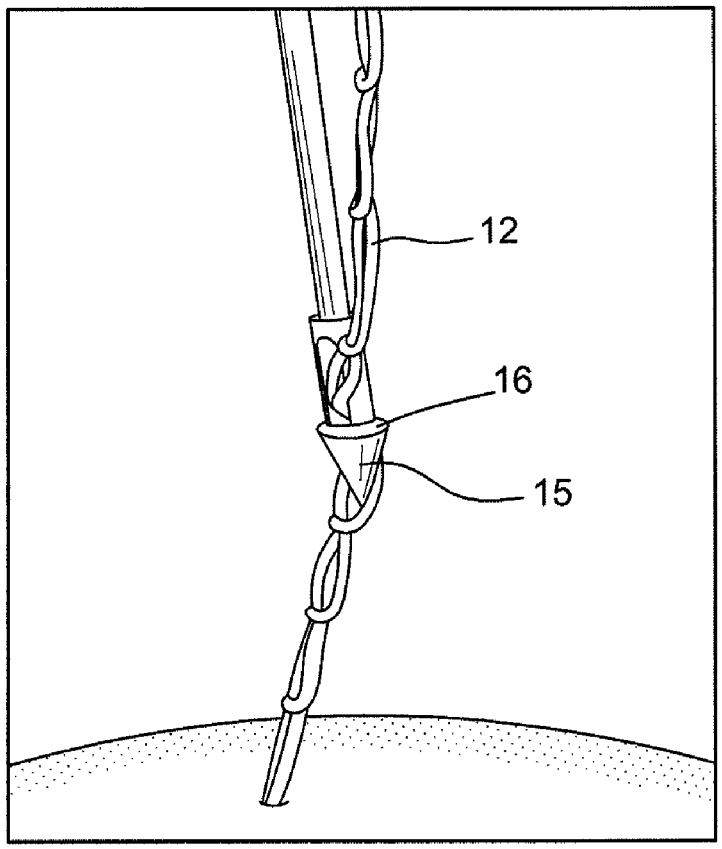
Figure 6:
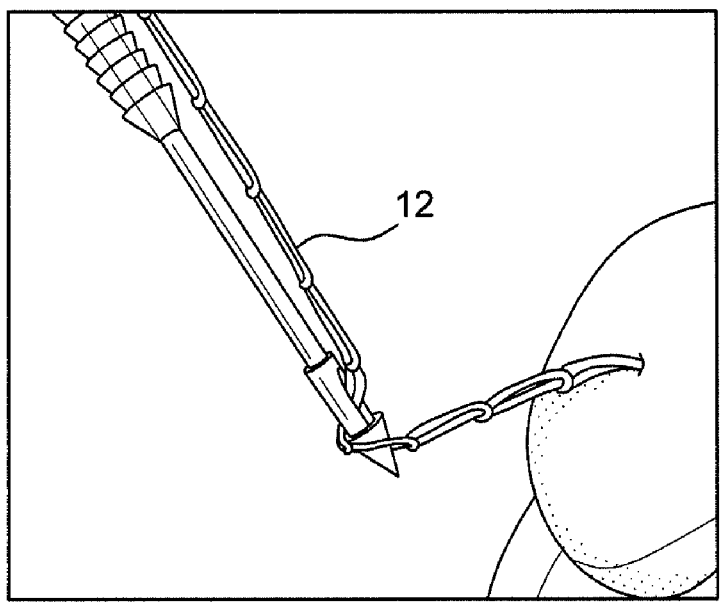
Figure 7:
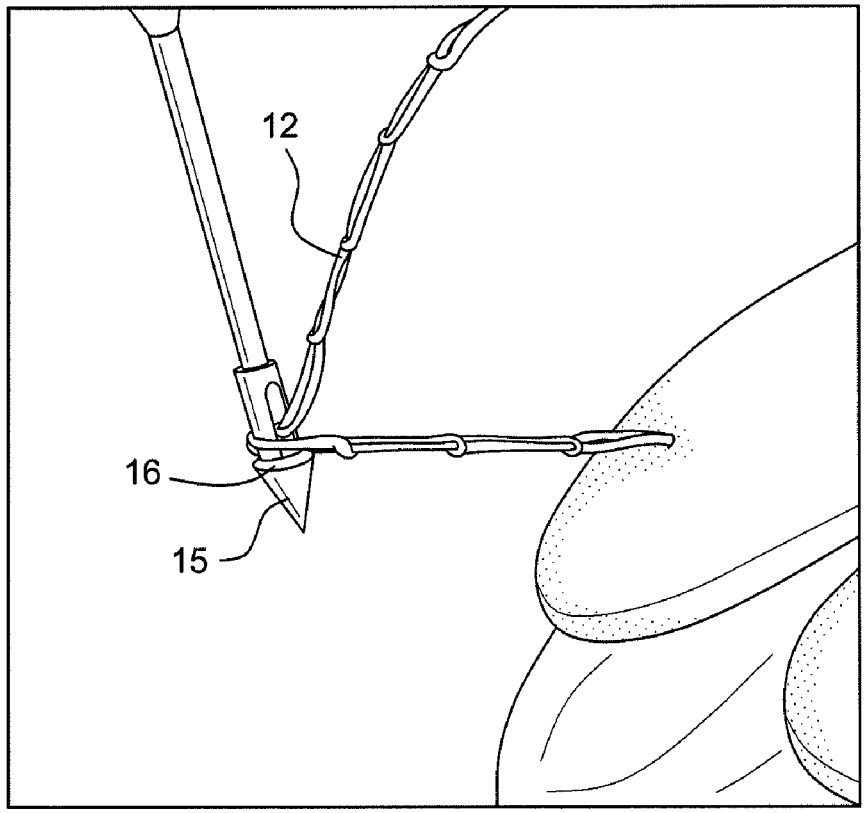

Next, referring to FIG. 4, the PushLock SP™ anchor 14 is advanced along the FiberChain® 12 and the PushLock SP™ anchor 14 is turned in a clockwise direction to bring the tip or implant 15 of the PushLock SP™ anchor 14 above a chosen link of the FiberChain® 12. Alternatively, the PushLock SP™ anchor may be advanced along the entire FiberChain®, without turning the PushLock SP™ anchor, but this may result in greater friction on the FiberChain®.

Figure 8:
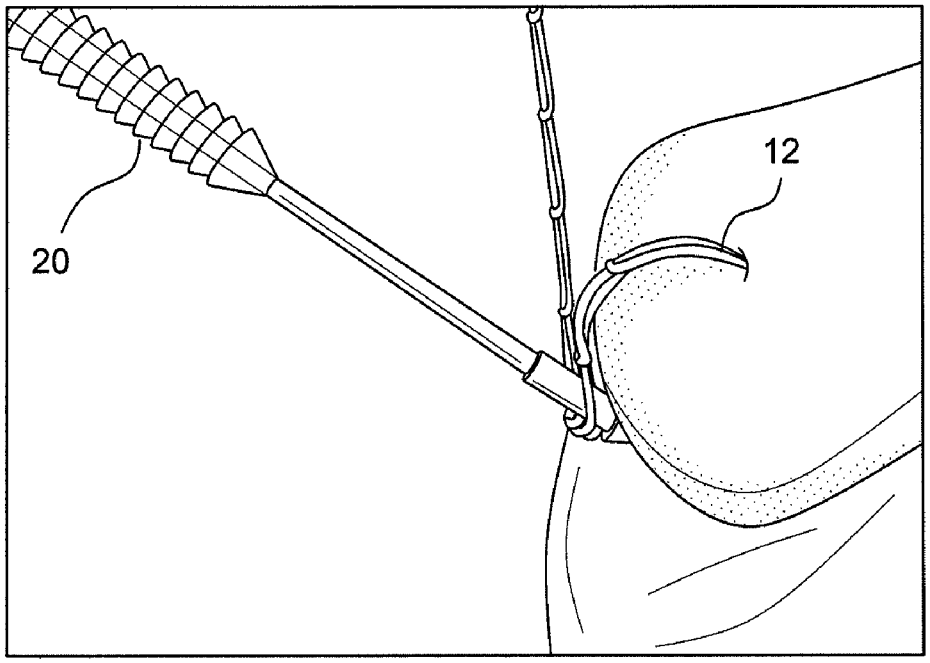

Referring to FIGS. 5-10, the tip 15 of the PushLock SP™ anchor 14 is pushed through the chosen link to capture both sides of the link above a shoulder 16 of the anchor tip 15, so PushLock SP™ anchor 14 securely captures the chosen link in place. Next, the tip 15 of the PushLock SP™ anchor 14 is pushed into a bone socket, as shown in FIG. 8. The PushLock SP™ anchor is then rotated to "reel in" the FiberChain® and thereby, provide an easy and adjustable way to tension the FiberChain® and to produce good compression over the top of the rotator cuff.

Figure 9:
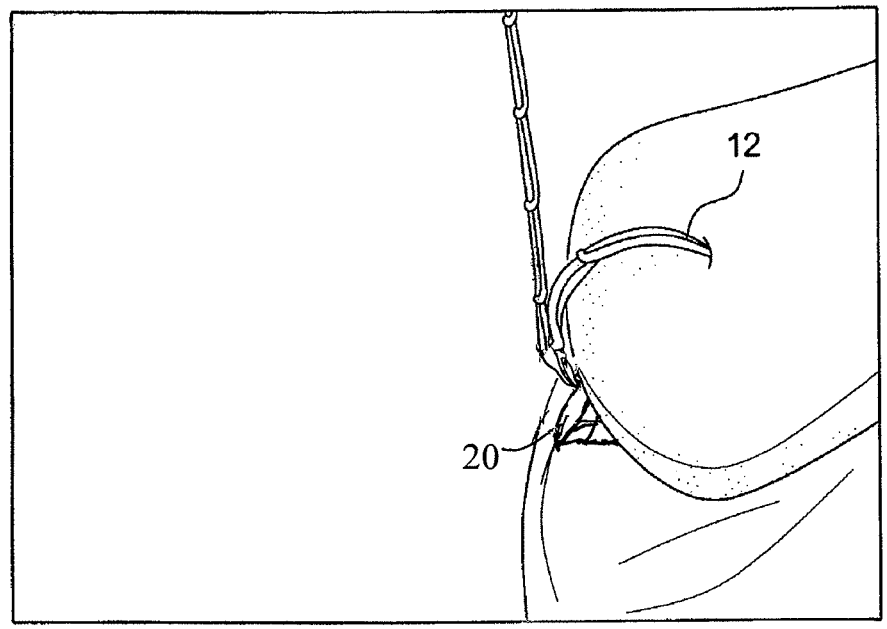
Figure 10:
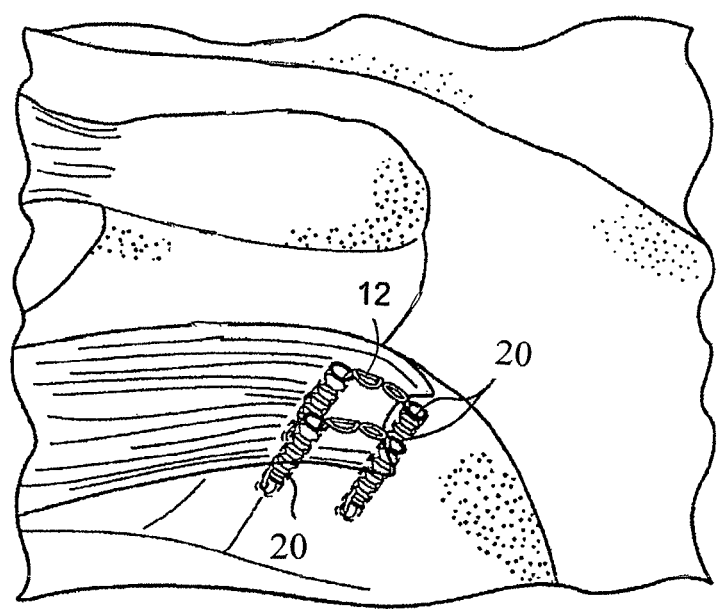

The fixation device or anchor 20 of the PushLock SP™ anchor is then impacted into the bone socket, using a standard PushLock technique, so that the anchor 20 advances and securely engages and locks the PushLock SP™ tip 15 and FiberChain® 12 in the bone socket (FIG. 9). After the anchor 20 is fully inserted in the bone socket, the ends of the FiberChain® 12 can be removed by clipping them short, leaving the graft securely fastened to bone. FIG. 10 illustrates a first medial row constructed with a first plurality of fixation devices 20 and a second lateral row constructed with a second plurality of fixation devices 20 with the suture chain 12 extending over the soft tissue.

A significant advantage of the present invention is that the sutures attached to the graft or the graft itself can be securely attached to the bone without the need to tie knots. Additionally, we can easily adjust the suture tension and achieve a hard stop, instead of a friction stop like in the push lock technique, and can thread through a single cannula.

Although the terms "chain," "suture chain" and Fiber-Chain® have been used interchangeably in this application, it must be understood that the term "chain" is not limited to only "suture chain" or FiberChain®; rather, the term "chain" encompasses a plurality of loops of any material and of any dimension (i.e., loops of similar or different diameters), as long as the loops are interconnected to each other. An exemplary suture chain that may be used in the present application is described in U.S. Patent Appl. Publ. No. 2007/0135843, the disclosure of which is incorporated by reference in its entirety herewith.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A method of tissue fixation comprising:
providing a suture chain that includes at least two loops formed of suture;
securing a first portion of the suture chain to a tissue to be fixated;
securing the suture chain to a fixation device by threading the suture chain through an eyelet of the fixation device;
rotating the fixation device to bring a tip of the fixation device above a chosen link of the suture chain;
capturing a loop of the suture chain with the same fixation device by pushing the tip of the fixation device through the chosen loop so that the tip locks the loop over a shoulder of the fixation device;
inserting the fixation device into a bone socket and subsequently tensioning the suture chain by rotating the fixation device to reel in the suture chain to properly position the tissue; and
anchoring the fixation device in the bone.

2. The method of claim 1, wherein the fixation device is a push-in type anchor.

3. The method of claim 1, wherein the fixation device is a swivel anchor with a tip configured to swivel relative to an anchor body.

4. A method of tissue fixation comprising:
providing a suture chain that includes at least two loops formed of and connected by suture;
providing a bone socket;
securing a first portion of the suture chain to a tissue to be fixated;
securing the suture chain to an anchor by threading the suture chain through an eyelet of the anchor;
subsequently, advancing the anchor along the suture chain by rotating the anchor to bring a tip of the anchor above a chosen link of the suture chain;
pushing the tip of the anchor through the chosen link to capture a loop of the suture chain so that the tip locks the loop over a shoulder of the anchor;
inserting the anchor with the captured loop into the bone socket;
rotating the anchor within the bone socket to reel in the suture chain and to tension the suture chain and properly position the tissue to be fixated; and
securing the captured loop and the anchor into the bone socket using a fixation device, thereby providing tissue fixation.

5. The method of claim 4, wherein the fixation device is a cannulated interference screw.

6. The method of claim 4, wherein the anchor is a push-in type anchor.

7. A method of attaching soft tissue to bone comprising:
providing a first medial row constructed with a first plurality of fixation devices, wherein at least one of the first fixation devices is an anchor pre-loaded with a suture chain that includes at least two loops formed of and connected by suture;
providing a second lateral row constructed with a second plurality of fixation devices, wherein at least one of the second fixation devices is a knotless fixation device, the knotless fixation device being configured to capture at least two different regions of the suture chain with two different elements of the knotless fixation device, and to secure the suture chain in a hole in bone;
positioning a tip of the knotless fixation device over a suture loop and pushing the tip through the suture loop so that the tip locks the loop over a shoulder of the anchor;
inserting the knotless fixation device and the locked loop into a bone socket;
rotating the knotless fixation device to reel in the suture chain and to tension the suture chain in the hole in bone; and
fully seating and securing the knotless fixation device with the locked loop in bone.

8. The method of claim 7, wherein the two different elements of the knotless fixation device are an eyelet and a shouldered tip.

9. The method of claim 7, wherein the anchor is a push-in type anchor.

10. A method of attaching soft tissue to bone comprising:
placing a medial anchor pre-loaded with a suture chain that includes at least two loops;
passing the suture chain through the soft tissue;
attaching the suture chain to a knotless fixation device by threading the suture chain through an eyelet of the knotless fixation device;
advancing the knotless fixation device over the suture chain to position the tip of the knotless fixation device over a suture loop;
pushing the tip through the suture loop so that the tip locks the loop over a shoulder of the body;
rotating the knotless fixation device to reel in the suture chain and to tension the suture chain to obtain a tensioned suture chain; and
securing the tensioned suture chain with the knotless fixation device in a hole in bone, the hole being provided lateral to the medial anchor.

11. The method of claim 10, wherein the suture chain provides both a hard stop that does not slip and frictional interference between the knotless fixation device and the bone socket.

* * * * *